United States Patent
Krishnan et al.

(10) Patent No.: US 9,665,687 B2
(45) Date of Patent: May 30, 2017

(54) ADAPTIVE IMAGING SYSTEM WORKFLOW AND USER INTERFACE SYSTEM

(75) Inventors: Srinivasan Krishnan, Schaumburg, IL (US); Steve D. Quam, Carpentersville, IL (US)

(73) Assignee: Siemens Healthcare GmbH (DE)

( * ) Notice: Subject to any disclaimer, the term of this patent is extended or adjusted under 35 U.S.C. 154(b) by 1196 days.

(21) Appl. No.: 13/019,363

(22) Filed: Feb. 2, 2011

(65) Prior Publication Data
US 2011/0271219 A1    Nov. 3, 2011

Related U.S. Application Data

(60) Provisional application No. 61/329,880, filed on Apr. 30, 2010.

(51) Int. Cl.
G06F 3/048 (2013.01)
G06F 19/00 (2011.01)

(52) U.S. Cl.
CPC ............... *G06F 19/3412* (2013.01)

(58) Field of Classification Search
None
See application file for complete search history.

(56) References Cited

U.S. PATENT DOCUMENTS 5,786,816 A * 7/1998 Macrae ............... G06F 19/325 128/920
2006/0219964 A1* 10/2006 Mochizuki ........... A61B 6/4494 250/580

OTHER PUBLICATIONS

J.H. Poore, "Markov Analysis of Software Specifications", ACM Transactions on Software Engineering and Methodology, vol. 2, No. 1, Jan. 1993, pp. 96-106.
Winfried Dulz, et al., "Calculating the Usage Probabilities of Statistical Usage Models by Constraints Optimization", AST '10, Proceedings of the 5th Workshop on Automation of Software Test, May 3-4, 2010, pp. 127-134.
S.J. Prowell, "Computations for Markov Chain Usage Models", Technical Report UT-CS-03-505.
J. H. Poore, et al., "A constraint-based approach to the representation of software usage models", Information and Software Technology 42 (2000), pp. 825-833.

* cited by examiner

*Primary Examiner* — Elaine Gort
*Assistant Examiner* — Rajiv Raj (57) ABSTRACT

A system configures a medical imaging system using utilization information. The system includes at least one repository storing records indicating usage and an associated time of usage, of particular features of a medical imaging system. A processor coupled to the at least one repository analyzes the records to determine, (a) frequency of usage of particular features of the medical imaging system and (b) a sequence of usage of the particular features of the medical imaging system and provide utilization data, by identifying in the records particular text strings using predetermined information associating predetermined text strings with corresponding features. An adaptation processor uses the utilization data to modify, delete or add a task to a task sequence employing the particular features. A display processor generates data representing at least one display image enabling a user to perform an adapted task sequence.

14 Claims, 9 Drawing Sheets

FIG. 2

Feature Parser

Select the system and date range of interest and click on parse to get the results.

System Serial: * All None   System Version: * All None   System Sector: * All None

** No selection of Hospital Country and Hospital Name will parse all the hospitals in the list
Hospital Country: None   Hospital Name: None

Date Range: * From: [ ▸ ] [ ▸ ]   To: [ ▸ ] [ ▸ ] [ ▸ ]

*** Changing any value above will clear all the previously parsed data.

[ Parse ]

ADAPTIVE IMAGING SYSTEM WORKFLOW AND USER INTERFACE SYSTEM

This is a non-provisional application of provisional application Ser. No. 61/329,880 filed Apr. 30, 2010, by S. D. Quam et al.

FIELD OF THE INVENTION

A system adaptively determines imaging system workflow and a user interface display in response to analysis of user utilization of system functions, errors and other system data.

BACKGROUND OF THE INVENTION

Known systems parse an error log to identify predetermined text patterns and provide the number of times a feature is invoked and analyze a workflow to attempt to resolve a problem reported by a customer and convert a customer workflow into a test script that can be deployed to reproduce the problem. However, known imaging systems fail to automatically adapt to a user environment and provide imaging system functions tailored to a user needs. A system according to invention principles addresses these deficiencies and related problems.

SUMMARY OF THE INVENTION

A system acquires information from usage information of an imaging system and dynamically changes a workflow and a User Interface for a particular site or a particular user. A system configures a medical imaging system using utilization information. The system includes at least one repository storing records indicating usage and an associated time of usage, of particular features of a medical imaging system. A processor coupled to at least one repository analyzes the records to determine, (a) frequency of usage of particular features of the medical imaging system and (b) a sequence of usage of the particular features of the medical imaging system and provide utilization data, by identifying in the records particular text strings using predetermined information associating predetermined text strings with corresponding features. An adaptation processor uses the utilization data to adapt a task sequence employing the particular features by at least one of, (i) changing a sequence of tasks a user is prompted with, (ii) adding a task to a task sequence of a user, (iii) deleting a task of a task sequence of a user and (iv) modifying a task of a task sequence of a user. A display processor generates data representing at least one display image enabling a user to perform an adapted task sequence.

DETAILED DESCRIPTION OF THE INVENTION

A system acquires information from user usage information of an imaging system and dynamically changes a workflow and a User Interface for a particular site or the user. The system analyzes a usage log indicating usage of individual functions of an imaging system (including, but not limited to, of an X-ray, MR (magnetic resonance), CT (computer tomography), Surgery (Operating Room), Hemo/EP (Hemodynamic/Electrophysiology) and ultrasound systems) and an error log of an imaging system. Thereby, the system understands how a particular user is using an imaging system and offers the user an option to select a new user interface (UI) display image compatible with the pattern of usage and frequency of usage of particular imaging system functions and reflecting user workflow. The system analyzes logs and imaging system function utilization records and employs automated test scripts derived based on customer usage patterns to dynamically adapt a workflow and user interface. The system adaptively parses error and function usage records to identify frequency of usage of particular features of an imaging system and buttons of a user interface of the imaging system and adaptively alters a task sequence (workflow) of a user and user interface display images to adapt the task sequence and images to optimize use of the features and user interfaces for a particular user system configuration and site. Multiple different sources of error and function usage records are analyzed including error logs, usage logs, email logs and activity logs. The information is analyzed using text parsing based on predetermined text strings identifying particular functions and features for example.

Figure 1:
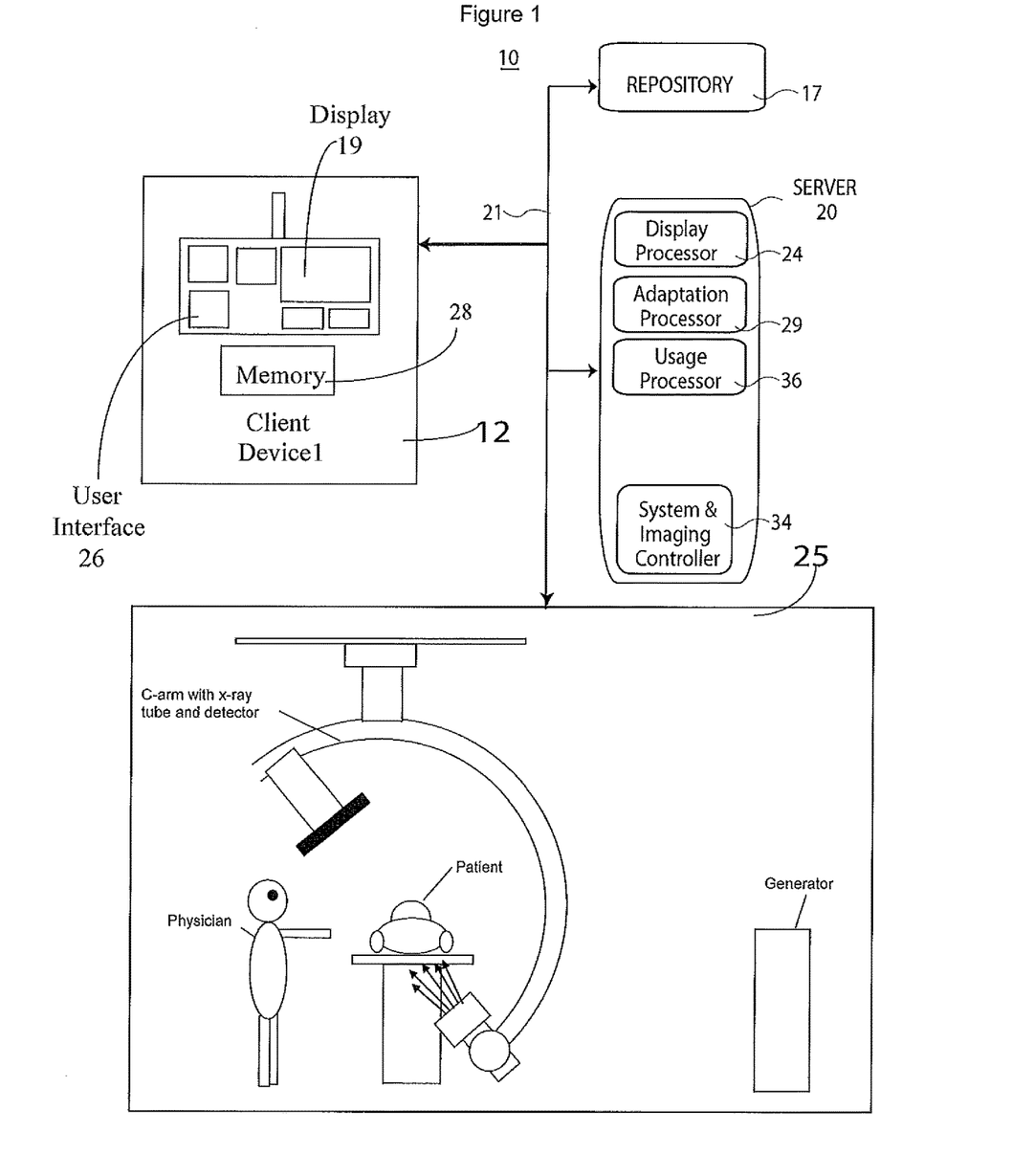
FIG. 1 shows a system for configuring a medical imaging system using utilization information, according to invention principles.

FIG. 1 shows system 10 for configuring a medical imaging system using utilization information. System 10 includes one or more processing devices (e.g., workstations or portable devices such as notebooks, Personal Digital Assistants, phones) 12 that individually include a user interface control device 26 such as a keyboard, mouse, touchscreen, voice data entry and interpretation device, display 19 and memory 28. System 10 also includes at least one repository 17, X-ray imaging modality system 25 (which in an alternative embodiment may comprise an MR (magnetic resonance), CT scan, or Ultra-sound system, for example) and server 20 intercommunicating via network 21. X-ray imaging modality system 25 comprises a C-arm that houses an X-ray radiation source device and a detector device mounted at different ends of the C-arm and rotating about a patient table. An associated electrical generator provides electrical power for the X-ray radiation system.

At least one repository 17 stores. error logs, usage logs, email logs and activity logs and medical image studies for multiple patients in DICOM compatible (or other) data format. A medical image study individually includes multiple image series of a patient anatomical portion which in turn individually include multiple images. Server 20 includes display processor 24, adaptation processor 29, usage processor 36 and system and imaging controller 34. Display 19 presents adaptively dynamically generated display images derived in response to imaging system usage characteristics and predetermined user (e.g., physician) specific preferences, comprising a Graphical User Interface (GUI). Imaging controller 34 controls operation of imaging device 25 in response to user commands entered via user interface 26. In alternative arrangements, one or more of the units in server 20 may be located in device 12 or in another device connected to network 21.

At least one repository 17, stores records indicating usage and an associated time of usage, of particular features of a medical imaging system. Usage processor 36 coupled to at least one repository 17 analyzes the records to determine, (a) frequency of usage of particular features of the medical imaging system and (b) a sequence of usage of the particular features of the medical imaging system and provide utilization data, by identifying in the records particular text strings using predetermined information associating predetermined text strings with corresponding features. Adaptation processor 29 uses the utilization data to adapt a task sequence employing the particular features by at least one of (i) changing a sequence of tasks a user is prompted with, (ii) adding a task to a task sequence of a user, (iii) deleting a task of a task sequence of a user and (iv) modifying a task of a task sequence of a user. Display processor 24 generates data representing at least one display image enabling a user to perform an adapted task sequence, System 10 employs derived function or feature frequency of use data to adjust a task sequence and to adapt an image displayed to a user. In one embodiment this is done automatically and in another a user is prompted with a new workflow or UI image change for selection. System 10 generates automated test scripts based on customer usage patterns to adapt a workflow and UI. A generated script alters a task sequence of a particular user for a particular day or until changed by a user. Alternatively, the system generates a script for altering a task sequence of a particular user in response to analysis of error and function logs over a day, for example. The sources of error and function usage records that are analyzed include error logs and function logs that record user interface button clicks by a user selecting features supported by the image system. Usage processor 36 analyzes the log information using text parsing based on predetermined text strings that identify particular functions. User actions are recorded in a structured way as part of error or other operation monitoring logs for error analysis and other diagnostic purposes. These logs are parsed to identify a predetermined set of user action pattern strings and the results of the parsed records are stored in repository 17 for further analysis.

System 10 adaptively and dynamically alters a task sequence by altering a sequence of user selectable function related buttons presented to a user in one or more displayed images, by altering a programmed sequence of events and functions or by altering a scheduled list of tasks of at least one worker or device.

System 10 does this by altering a navigation sequence of display images presented to a user for performing X-ray imaging, in response to detecting a user is performing for the majority or substantially all of the time, Angiography or Limb imaging, for example. Angiography provides a UI and task sequence supporting fluoroscopy, mask acquisition, contrast administration and DSA (digital subtraction angiography) imaging and subtraction and excluding tasks associated with patient table movement for limb imaging, for example. Limb imaging (such as for an orthopedic surgeon) supports patient table movement operations and tasks and excludes DSA specific imaging tasks, for example. Once a task sequence becomes a preferred sequence for a user, the user is asked, if the sequence should be preserved for future tasks. On confirmation, frequently used user interface elements are re-positioned (if necessary) for a subsequent user action.

Figure 2:
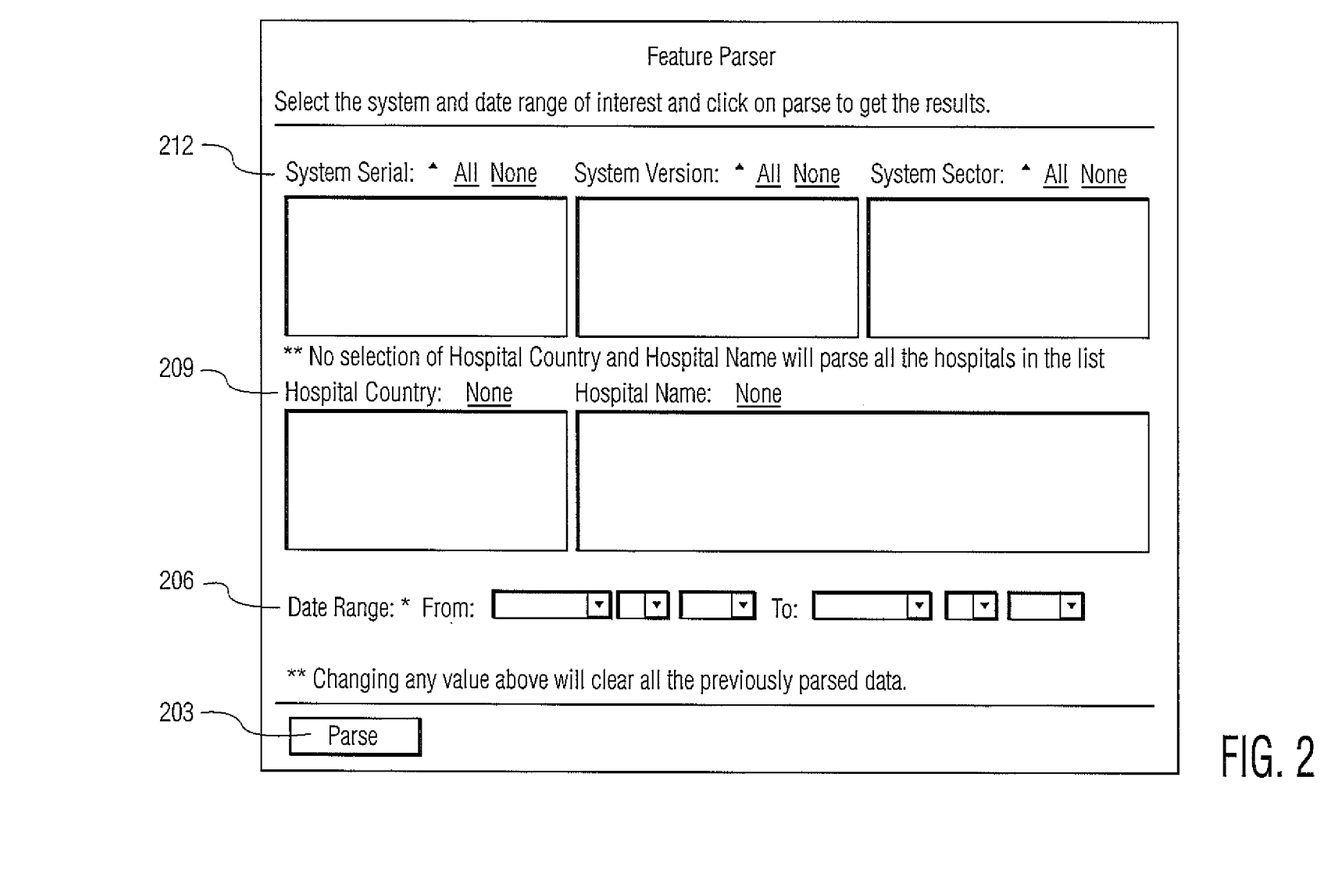
FIG. 2 shows a user interface display image window enabling a user to parse and access medical imaging system utilization information, according to invention principles.
Figure 3:
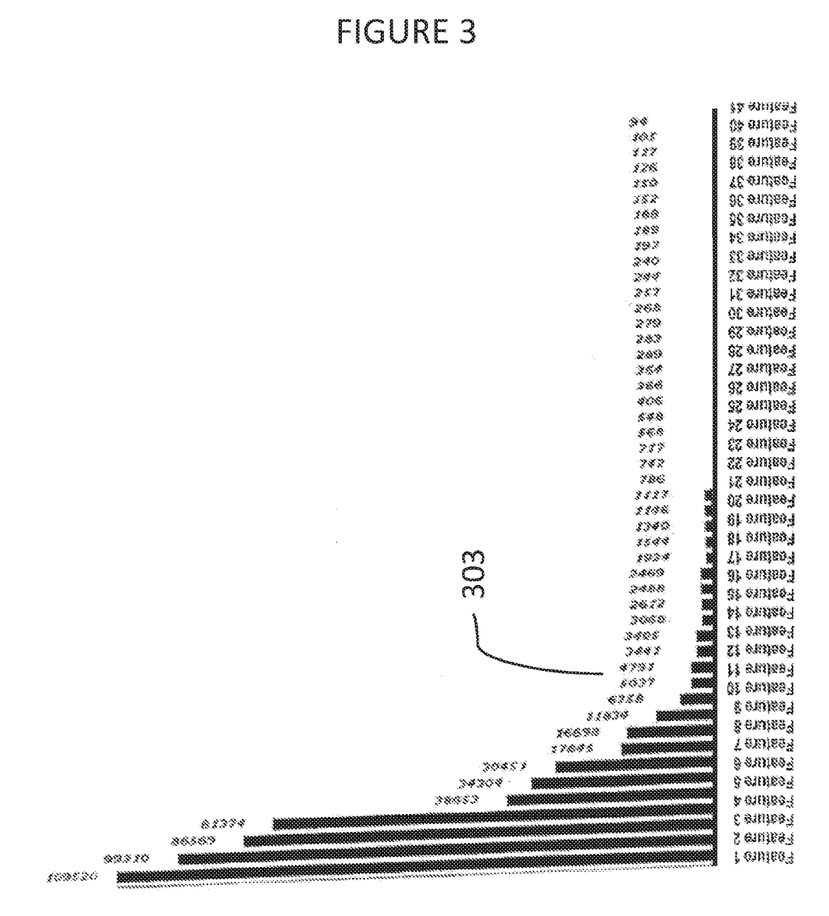
FIG. 3 shows a chart presenting utilization information indicating the number of times individual features of a medical imaging system are used in a predetermined time period, according to invention principles.

FIG. 2 shows a user interface display image window enabling a user to parse and access medical imaging system utilization information. A user employs the FIG. 2 UI image to initiate a search via button 203 by usage processor 36 to provide an overview of system utilization and clinical workflow activities for a particular date range (entered via data field line 206), hospital country and name (entered via data field line 209) and system serial number, version and sector (entered via data field line 212). FIG. 3 shows a chart presenting feature utilization information indicating the number of times individual features of a medical imaging system are used in a predetermined time period. The chart is derived using feature utilization data acquired from log files in repository 17 and shows that an Annotate Text List function 303 is used 5,037 times in a predetermined time period, for example.

Figure 6:
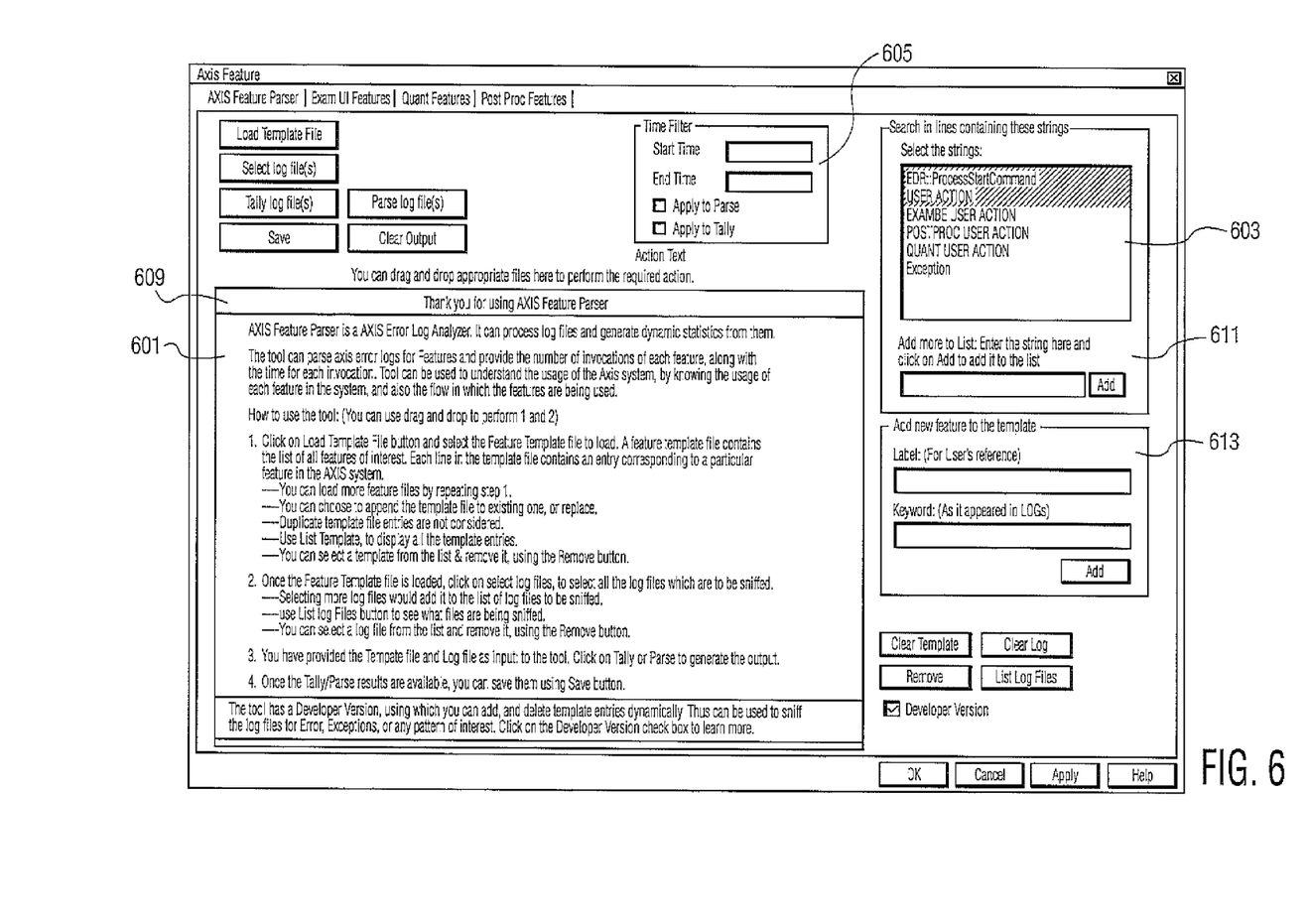
FIG. 6 shows a user interface display image window enabling a user to search and access medical imaging system utilization information, according to invention principles.

Usage processor 36 searches utilization log files for information requested via the user interface display image window of FIG. 2 or requested via FIG. 6 search window 601. FIG. 6 shows user interface display image window 601 enabling a user to search and access medical imaging system utilization information stored in repository 17. A user selected template log file presented in area 609 showing feature utilization activity records is searched to find text search strings entered by a user in area 603, The utilization records for a date range entered in area 605 are searched for the text strings and a label or keyword entered via elements 611 and 613. Usage processor 36 searches multiple utilization log files by parsing the log file records stored during a predetermined time period. The search is performed in a hierarchical manner by identifying lines in the log files containing a generic text string (a label) and searching the resultant identified lines for a specific text string or text string pattern.

Figure 4:
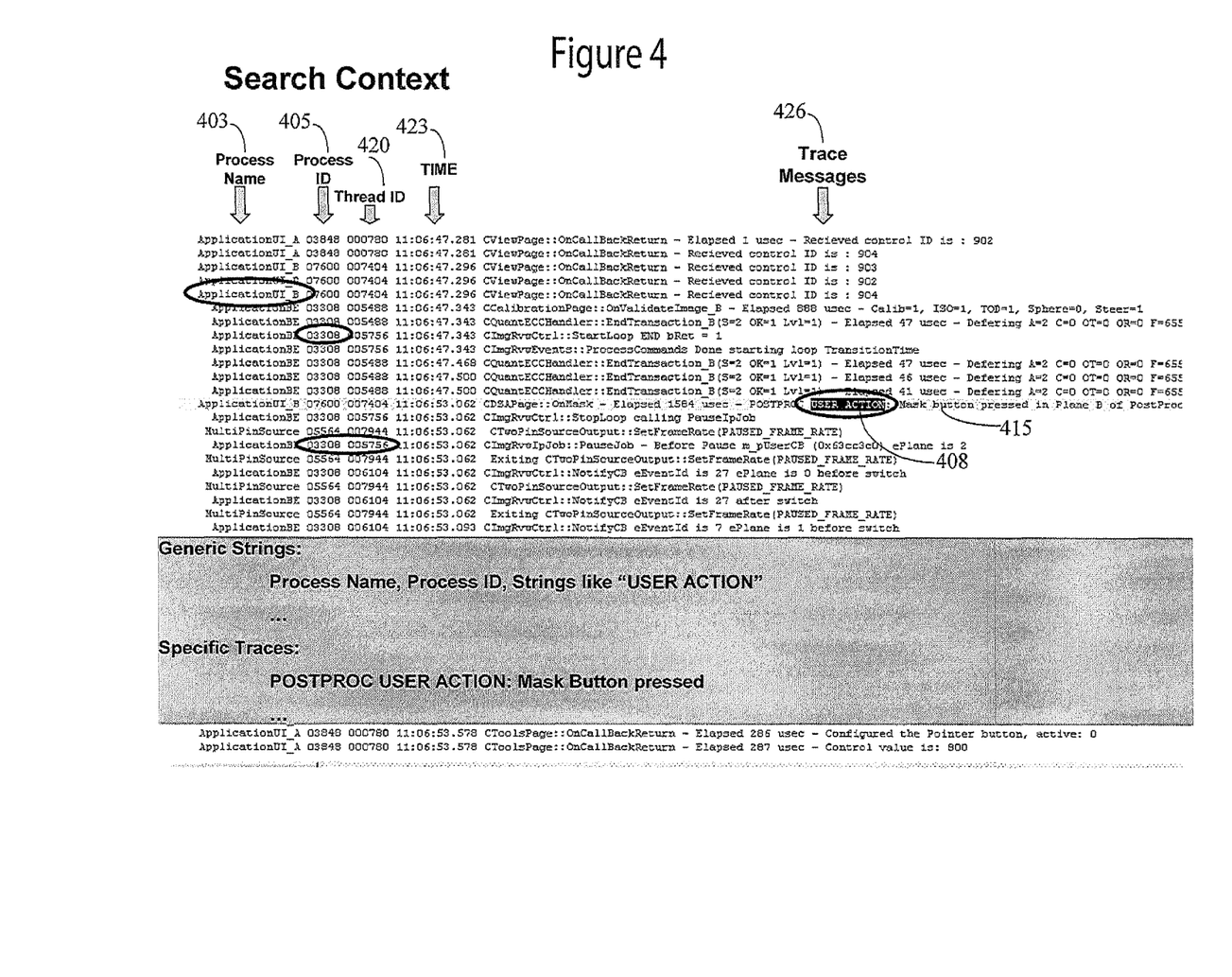
FIG. 4 illustrates search of a log file of utilization information indicating usage and context of selection of individual features of a medical imaging system in a predetermined time period, according to invention principles.

FIG. 4 illustrates search of a log file of utilization information indicating usage and context of selection of individual features of a medical imaging system in a predetermined time period. The log file includes individual records on each line indicating utilization of an individual imaging system feature and context in which a feature is selected by a user. The context is indicated by records of the sequence of preceding selection features and commands as well as subsequently selected features and commands. An individual record includes ProcessName 403, Process ID 405, Thread ID 420, Time 423 and Trace Message 426. Usage processor 36 (FIG. 1) searches utilization log files by parsing the log file records to identify lines including a generic text string such as Process Name 403, Process ID 405, and text string "User Action" 408. Usage processor 36 further searches record lines previously identified using a generic text string, by parsing the identified line records to identify a specific text string such as text string "Postproc User Action: Mask Button pressed" 415.

Figure 5:
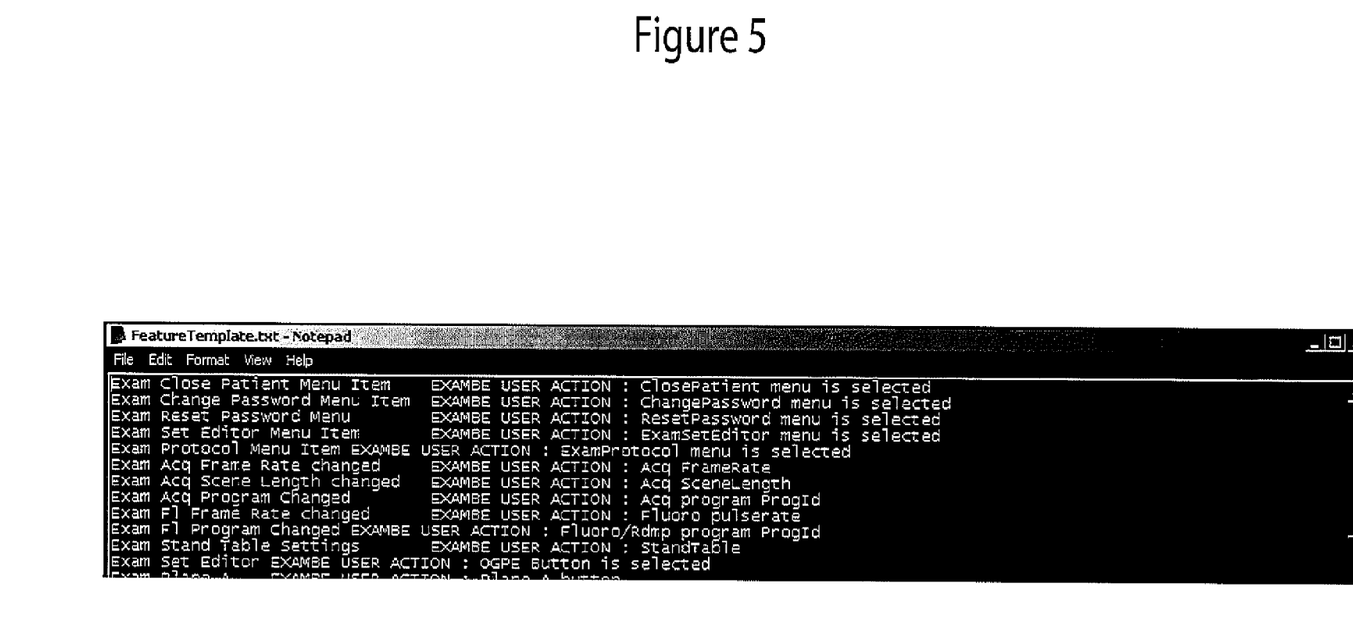
FIG. 5 illustrates format of a template file of search terms for searching utilization information indicating usage and context of selection of individual features of a medical imaging system in a predetermined time period, according to invention principles.
Figure 7:
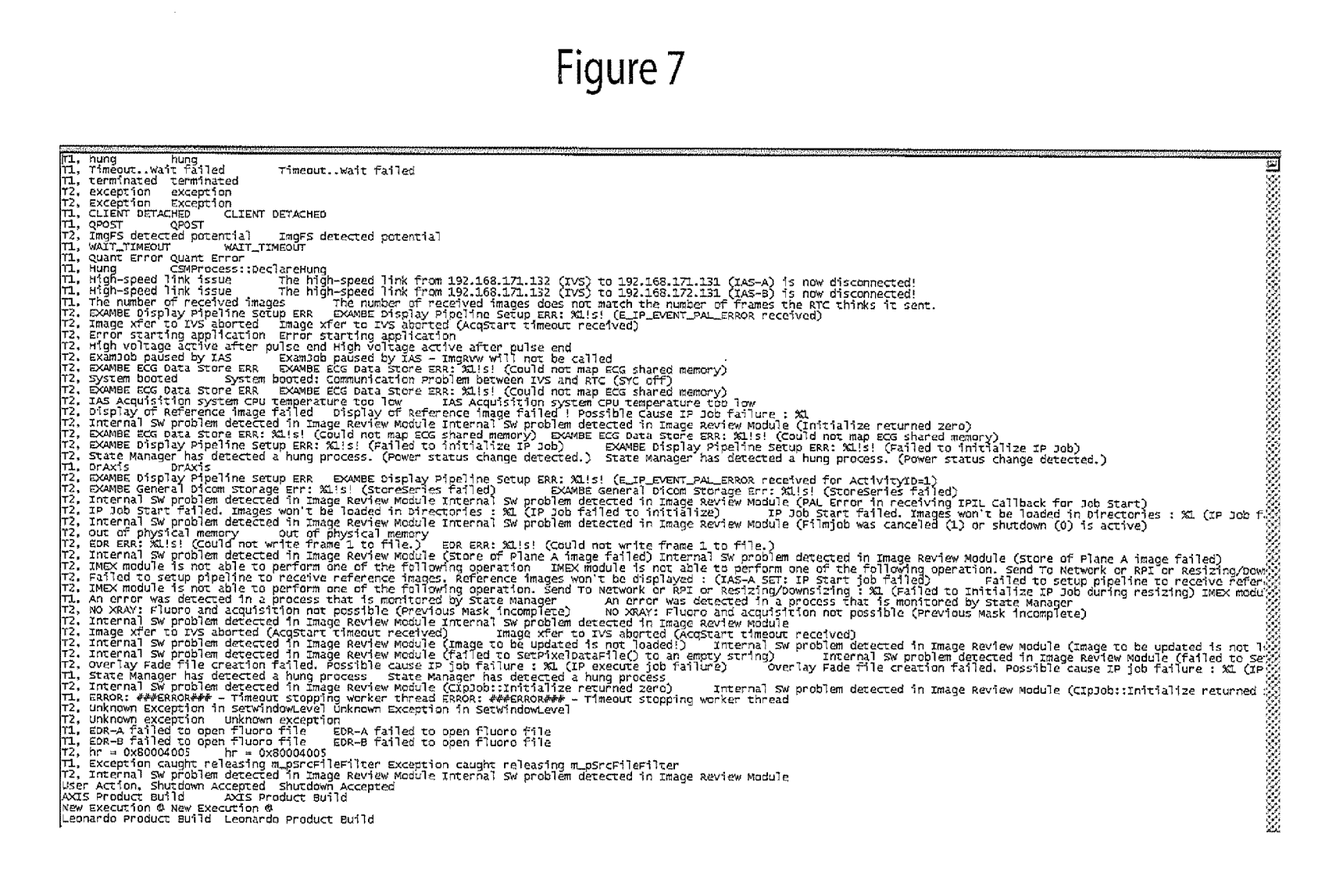
FIG. 7 illustrates an error log file including error messages and system and indicating user actions of a medical imaging system in a predetermined time period, according to invention principles.

FIG. 5 illustrates format of a template search term file of generic and specific search terms that are used by usage processor 36 to search utilization information indicating usage and context of selection of individual features of a medical imaging system in a predetermined time period. Usage processor 36 employs individual search terms selected in response to user command or predetermined in response to system configuration. Usage processor 36 alternatively employs all search terms in the template file for searching utilization records. The generic and specific template file search terms are in the format of a Label:Keyword pair where a Keyword is an exact text string to be searched and a Label is a representation of the respective Keyword. A Label: Keyword pair comprises "USER ACTION : ClosePatient menu is selected 503", for example. Each line of the template search term file contains a Label:Keyword pair. Usage processor 36 searches utilization information for the Label:Keyword pairs associated with a specific type of workflow task sequence (e.g., for an Angiography procedure) in a template file specific to the specific workflow task sequence. This provides data indicating how the medical imaging system has been used. Usage processor 36 determines a tally indicating the number of occurrences for each label:keyword pair in imaging system utilization information. This enables processor 36 to determine how many times each feature is being used and to generate chart data as illustrated in FIG. 1 Usage processor 36 uses search data associated with a specific workflow task sequence to determine medical system utilization for the specific workflow task sequence specific to the keywords. Adaptation processor 29 adapts a task sequence employing the medical imaging system features associated with the search data by changing a sequence of tasks a user is prompted with, adding a task to a task sequence of a user, deleting a task of a task sequence of a user and/or modifying a task of a task sequence of a user. Processor 29 adapts a specific type of workflow task sequence to improve operating efficiency of the workflow to minimize user interactions and time to perform a specific workflow by adjusting order of tasks and user selectable buttons presented in user interface windows in response to utilization data search results. The search results indicate an order and frequency of use of system features and selectable buttons as well as the number of time a feature or button or other image element is used. Usage processor 36 analyzes both utilization and error log file records, to determine frequency and sequence of usage of particular features of the medical imaging system and errors associated with a particular type of workflow. FIG. 7 illustrates an error log file including error messages (e.g., labeled T1, T2, T3 and so on to indicate error severity and type) of a medical imaging system with one error message per line in sequential time order over a predetermined time period. Processor 36 searches utilization records for workflow specific search terms (label:keyword term pairs) using a workflow specific template search file including search terms specific to a particular type of workflow task sequence. Processor 36 searches error records for error data associated with the specific workflow using a workflow specific error template search file including error search terms specific to a particular type of workflow task sequence. Processor 36 identifies in the utilization and error records, particular text strings using predetermined search term information associating predetermined text strings with corresponding features in the workflow and error search term template files. In one embodiment individual error records are associated with a particular workflow type and rated to indicate type and degree of impact on a workflow.

Adaptation processor 29 uses the utilization data and error data derived by a search to adapt a task sequence employing particular features by, changing a sequence of tasks a user is prompted with, adding a task to a task sequence of a user, deleting a task of a task sequence of a user and modifying a task of a task sequence of a user. Different error search term template files are used, for identifying errors and exception conditions and functions and features of a particular type of workflow task sequence. Usage processor 36 periodically stores utilization and error log files in a database such as repository 17. In one embodiment, the database and a web interface are customized to provide results for an individual site or imaging system configuration. The system is used for combination workflow task sequences including both imaging system and patient monitoring tasks.

Figure 8:
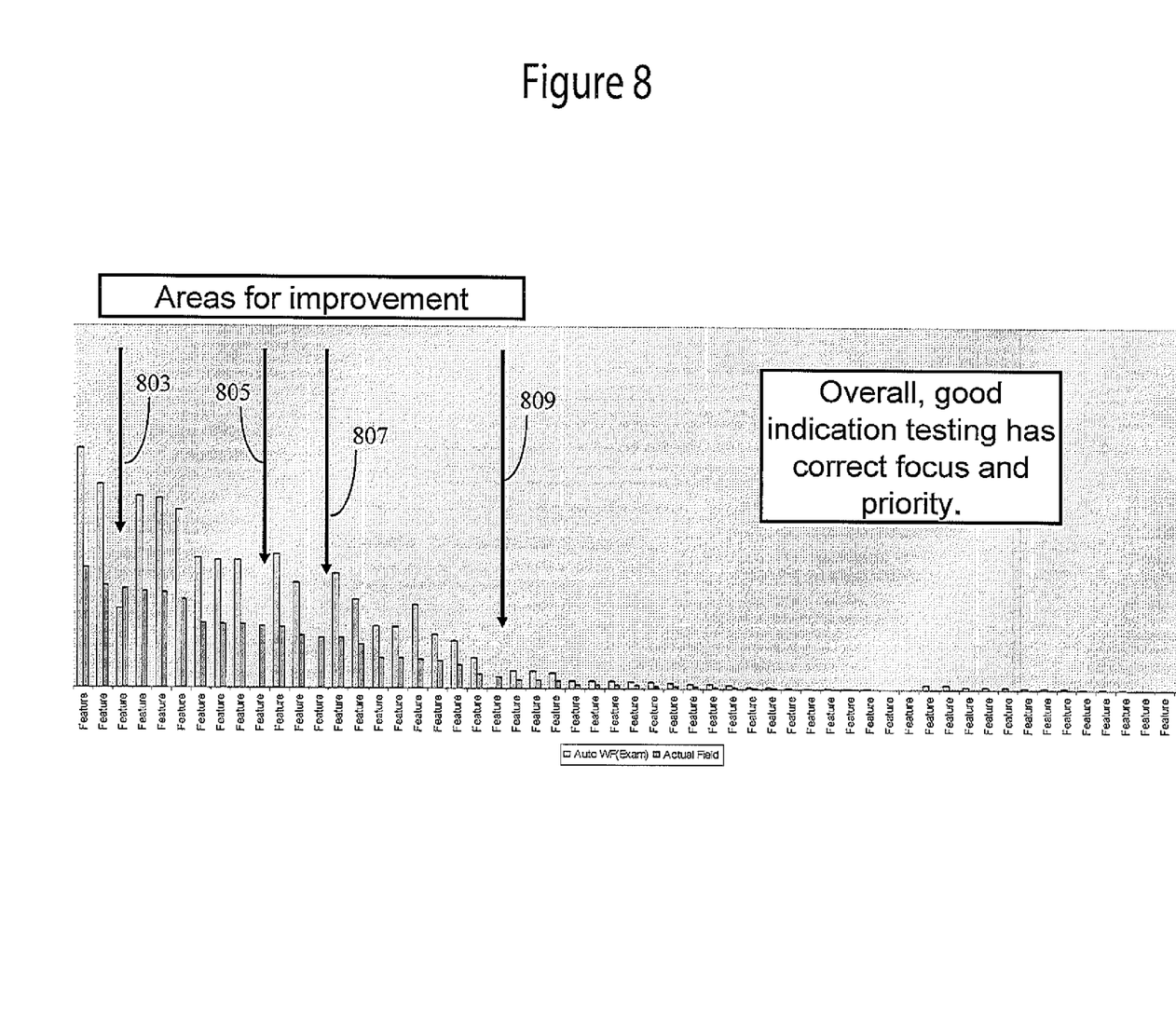
FIG. 8 shows a chart comparing utilization information indicating the number of times individual features of a medical imaging system are used in a predetermined automated specific workflow and the corresponding number of time features are used in a corresponding workflow in the field, according to invention principles.

FIG. 8 shows a chart comparing utilization information indicating the number of times individual features of a medical imaging system are used (light bars in Figure) in a predetermined automated specific type of workflow and the corresponding number of times features are used (darker bars in Figure) in a corresponding workflow actually employed by a user in practice. The darker bars 805, 807 and 809 indicate features that are employed by a user but are absent from the predetermined automated workflow. Bar 803 indicates a feature that is employed by a user in practice more often than is expected by the predetermined automated workflow. Usage processor 36 automatically identifies that the predetermined automated workflow does not employ features associated with bars 805, 807 and 809 and that the frequency of use of the feature associated with bar 803 is not reflected in the automated workflow. Adaptation processor 29 automatically adapts the task sequence of the predetermined automated workflow to include tasks to use the missing features of bars 805, 807 and 809 and to change the automated workflow and associated UI images to more optimally reflect increased frequency of use of the task associated with bar 803.

Figure 9:
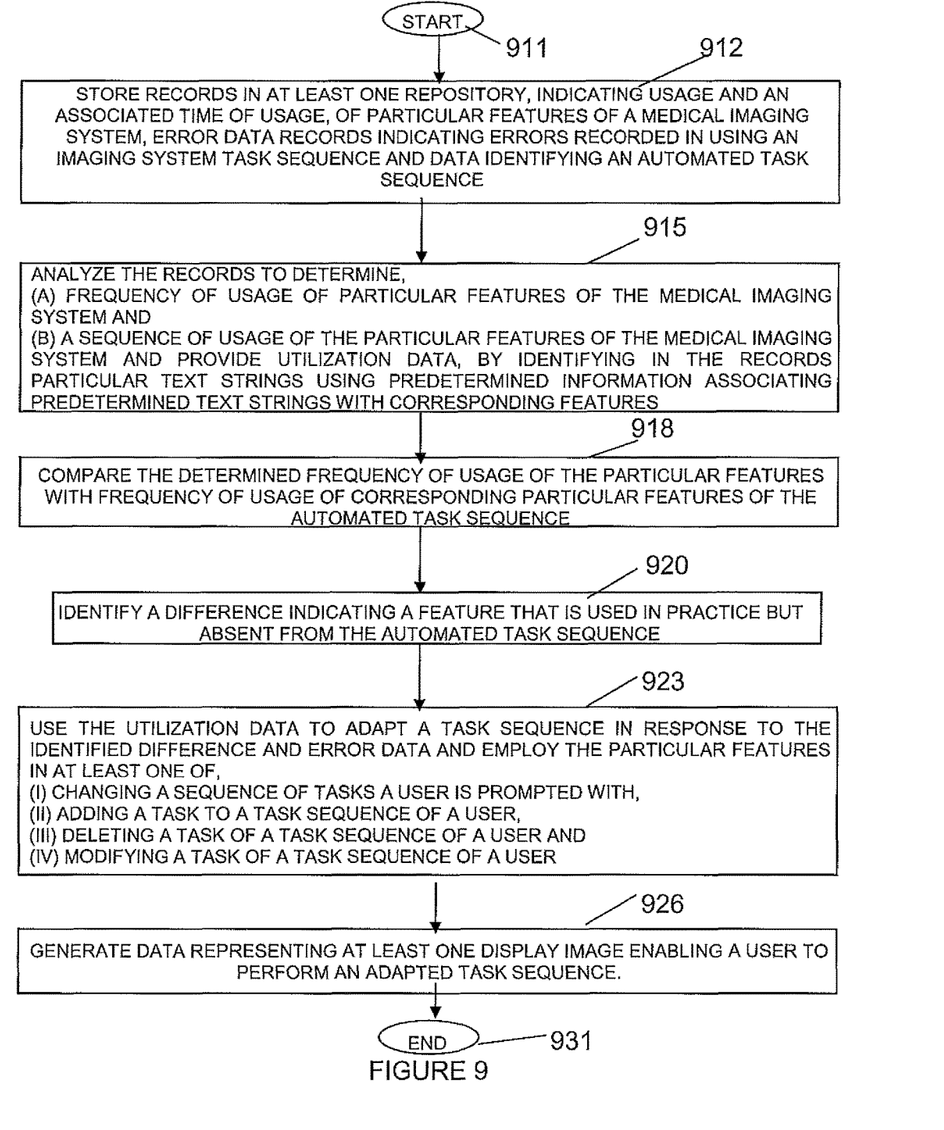
FIG. 9 shows a flowchart of a process used by a system for configuring a medical imaging system using utilization information, according to invention principles.

FIG. 9 shows a flowchart of a process used by system 10 (FIG. 1) for configuring a medical imaging system using utilization information. In step 912 following the start at step 911, usage processor 36 stores records in at least one repository 17, indicating usage and an associated time of usage, of particular features (comprising functions) of a medical imaging system, error data records indicating errors recorded in using an imaging system task sequence and data identifying an automated task sequence. Usage processor 36 in step 915 analyzes the records to determine, (a) frequency of usage of particular features of the medical imaging system and (b) a sequence of usage of the particular features of the medical imaging system, and provide utilization data, by identifying in the records particular text strings using predetermined information associating predetermined text strings with corresponding features. Processor 36 in step 918 compares the determined frequency of usage of the particular features with frequency of usage of corresponding particular features of the automated task sequence. In step 920 processor 36 identifies a difference indicating a feature that is used in practice but absent from the automated task sequence, or used more frequently in practice than in, an automated task sequence.

Adaptation processor 29 in step 923 uses the utilization data and/or the error data to adapt a task sequence employing the particular features or user interface image and/or adapt the task sequence or user interface image in response to the identified difference (e.g., by adding the absent feature) and automatically initiates system update to incorporate the adapted task sequence. Adaptation processor 29 employs the particular features to adapt the task sequence by at least one of, (i) changing a sequence of tasks a user is prompted with, (ii) adding a task to a task sequence of a user, (iii) deleting a task of a task sequence of a user and (iv) modifying a task of a task sequence of a user. Adaptation processor 29 uses the utilization data to adapt user selectable functions provided in a display image in response to the utilization data. Processor 29 uses the utilization data to adapt user selectable functions provided in a display image by at least one of, (i) changing a sequence of image elements a user is prompted with, (ii) adding a user interactive image element to a display image presented to a user, (iii) deleting a user interactive image element in a display image presented to a user and (iv) modifying a user interactive image element in a display image presented to a user. In step 926, display processor 24 generates data representing at least one display image prompting a user with an option to employ an adapted task sequence and enabling a user to perform the adapted task sequence. The process of FIG. 9 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user A user interface (UI), as used herein, comprises one or more display images, generated by a user interface processor and enabling user interaction with a processor or other device and associated data acquisition and processing functions. The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-9 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes a usage log indicating actual usage of individual functions of an imaging system, compares the actual usage with a predetermined automated workflow, identifies differences including functions that are used in practice but absent from the automated workflow as well as features in the automated workflow used more or less than expected and modifies the automated workflow to add missing tasks and function and to modify user interfaces to adapt to different frequency of use of a function. Further, the processes and applications may, in alternative embodiments, be located on one or more (e.g., distributed) processing devices on a network linking the units of FIG. 1. Any of the functions and steps provided in FIGS. 1-9 may be implemented in hardware, software or a combination of both.

What is claimed is:

1. A system for configuring a medical imaging system using utilization information, comprising:
    an imaging controller configured to control operation of an imaging device to perform particular imaging system functions according to a task sequence to acquire imaging data;
    at least one repository storing records indicating usage and an associated time of usage, of said particular imaging system functions performed on the imaging device;
    a usage processor coupled to said at least one repository configured to analyze said records to:
        determine, (a) frequency of usage of said particular imaging system functions, and (b) a sequence of usage of said particular imaging system functions, and
        provide utilization data, by identifying in said records particular text strings using predetermined information associating predetermined text strings with corresponding imaging system functions;
    an adaptation processor configured to use the utilization data to create an adapted task sequence which minimizes user interactions and time to perform said particular imaging system functions, wherein creation of the adapted task sequence is performed by at least one of,
        (i) changing a sequence of tasks a user is prompted with,
        (ii) adding a task to a respective task sequence of said user,
        (iii) deleting a task of said respective task sequence of said user and
        (iv) modifying a task of said respective task sequence of said user; and a display processor configured to:
  present at least one image corresponding to the adapted task sequence on a user interface device, and
  in response to receiving user-selection of the adapted task sequence, perform the particular imaging system functions according to the adapted task sequence using the imaging controller.

2. A system according to claim 1, wherein said data representing said at least one display image prompts said user with an option to employ the adapted task sequence.

3. A system according to claim 1, wherein
said adaptation processor automatically initiates system update to incorporate said adapted task sequence.

4. A system according to claim 1, wherein
said adaptation processor uses the utilization data to adapt user selectable functions provided in a respective display image in response to the utilization data.

5. A system according to claim 4, wherein
said adaptation processor uses the utilization data to adapt the user selectable functions provided in the respective display image by at least one of,
  (i) changing a sequence of image elements a user is prompted with,
  (ii) adding a first user interactive image element to a first display image presented to a first user,
  (iii) deleting a second user interactive image element in a second display image presented to a second user, and
  (iv) modifying a third user interactive image element in a third display image presented to a third user.

6. A system according to claim 1, wherein
said usage processor compares the determined frequency of usage of said particular imaging system functions with frequency of usage of corresponding particular features of an automated workflow process, identifies a difference indicating an absent feature that is used in practice but absent from the automated workflow process, and
said adaptation processor adapts said task sequence to add a task employing the absent feature, in response to the identified difference.

7. A system according to claim 1, wherein
said usage processor compares the determined frequency of usage of said particular imaging system functions with frequency of usage of corresponding particular features of an automated workflow process, identifies a difference indicating a respective imaging system function that is used more frequently in practice than in an automated task sequence, and
said adaptation processor adapts said task sequence or a user interface image, in response to the identified difference.

8. A system according to claim 1, wherein
said at least one repository stores error data records indicating errors recorded in using said task sequence,
said adaptation processor uses both the utilization data and the error data to adapt said task sequence employing said particular features.

9. A system for configuring a medical imaging system using utilization information, comprising:
  an imaging controller configured to control operation of an imaging device to perform particular imaging system functions according to a task sequence to acquire imaging data;
  at least one repository storing records indicating usage and an associated time of usage, of said particular imaging system functions and data identifying an automated task sequence for operating the imaging device;
  a usage processor coupled to said at least one repository configured to:
    analyze said records to determine frequency of usage of particular imaging system functions,
    compare the determined frequency of usage of said particular imaging system functions with frequency of usage of corresponding particular features of said automated task sequence,
    identify a difference indicating a respective imaging system function that is used in practice but absent from said automated task sequence; and
  an adaptation processor configured to create an adapted task sequence which minimizes user interactions and time to perform said automated task sequence, in response to the identified difference, by at least one of,
    (i) changing a sequence of tasks a user is prompted with,
    (ii) adding a task to a task sequence of a user,
    (iii) deleting a task of a task sequence of a user, and
    (iv) modifying a task of a task sequence of a user; and
  a display processor configured to:
    present at least one image corresponding to the adapted task sequence on a user interface device, and
    in response to receiving user-selection of the adapted task sequence, perform the particular imaging system functions according to the adapted task sequence on the imaging device.

10. A system according to claim 9, wherein
said usage processor determines a sequence of usage of said particular imaging system functions and provides utilization data, by identifying in said records particular text strings using predetermined information associating predetermined text strings with corresponding features.

11. A system according to claim 10, wherein
said at least one repository stores error data records indicating errors recorded in using an imaging system task sequence,
said adaptation processor uses both the utilization data and the error data to adapt said task sequence employing said particular features.

12. A computer-implemented method for configuring a medical imaging system using utilization information, comprising:
  using an imaging controller to control operation of an imaging device to perform particular imaging system functions according to a task sequence to acquire imaging data;
  storing records in at least one repository, indicating usage and an associated time of usage, of said particular imaging system functions performed on the imaging device;
  analyzing, by a usage processor of a computer, said records to determine,
    (a) frequency of usage of particular imaging system functions, and
    (b) a sequence of usage of said particular imaging system functions and provide utilization data, by identifying in said records particular text strings using predetermined information associating predetermined text strings with corresponding imaging system functions;
  using, by the usage processor, the utilization data to create an adapted task sequence which minimizes user interactions and time to perform said particular imaging system functions wherein creation of the adapted task sequence is performed by at least one of,
(i) changing a sequence of tasks a user is prompted with,
(ii) adding a task to a task sequence of a user,
(iii) deleting a task of a task sequence of a user, and
(iv) modifying a task of a task sequence of a user; and
presenting at least one image corresponding to the adapted task sequence on a user interface device, and
in response to receiving user-selection of the adapted task sequence, performing the particular imaging system functions according to the adapted task sequence on the imaging device.

13. A computer-implemented method according to claim 12, further comprising:
storing in said at least one repository, data identifying an automated task sequence,
comparing the determined frequency of usage of said particular imaging system functions with frequency of usage of corresponding particular features of said automated task sequence,
identifying a difference indicating a feature that is used in practice but absent from said automated task sequence, and
adapting said task sequence in response to the identified difference.

14. A computer-implemented method according to claim 12, further comprising:
storing in said at said least one repository, error data records indicating errors recorded in using an imaging system task sequence, and
adapting said task sequence in response to the error data records.

* * * * *